United States Patent [19]
Alt

[11] Patent Number: 5,433,730
[45] Date of Patent: Jul. 18, 1995

[54] CONDUCTIVE POUCH ELECTRODE FOR DEFIBRILLATION

[75] Inventor: Eckhard Alt, Ottobrunn, Germany

[73] Assignee: Intermedics, Inc., Angleton, Tex.

[21] Appl. No.: 133,654

[22] Filed: Oct. 7, 1993

Related U.S. Application Data

[63] Continuation-in-part of Ser. No. 937,173, Aug. 31, 1992, which is a continuation-in-part of Ser. No. 517,186, May 1, 1990, Pat. No. 5,143,089.

[51] Int. Cl.⁶ .................................................. A61N 1/39
[52] U.S. Cl. .......................................... 607/5; 607/36; 607/123
[58] Field of Search ................. 607/5, 36, 37, 40, 116, 607/119, 122, 123

[56] References Cited

U.S. PATENT DOCUMENTS

| | | | |
|---|---|---|---|
| 3,683,933 | 8/1972 | Mansfield | 607/36 |
| 3,735,766 | 5/1973 | Bowers et al. | 607/36 |
| 4,013,081 | 3/1977 | Kolenik | 607/36 |
| 5,220,929 | 6/1993 | Merquit | 607/36 X |

FOREIGN PATENT DOCUMENTS

9220402  11/1992  WIPO ................................. 607/36

*Primary Examiner*—Lee S. Cohen
*Attorney, Agent, or Firm*—O'Connor Cavanagh

[57] ABSTRACT

An implantable defibrillator includes a waveform generator having a metal housing for the generator electronics. The housing is used as one of the electrodes for cardioversion and defibrillation of the chambers of the patient's heart. An electrically conductive pouch having an effective electrical surface area considerably larger than its geometric surface area is constructed to receive and partially surround the generator, and to make electrical connection with its metal housing to enhance the conductivity of the housing as an electrode. An extension lead is electrically connected to the pouch to further enhance the electric field established during defibrillation.

26 Claims, 2 Drawing Sheets

CONDUCTIVE POUCH ELECTRODE FOR DEFIBRILLATION

CROSS-REFERENCE TO RELATED APPLICATION

This application is a continuation-in-part of copending U.S. patent application Ser. No. 07/937,173, filed Aug. 31, 1992, which is a continuation-in-part of Ser. No. 07/517,186, filed May 1, 1990, now U.S. Pat. No. 5,143,089, issued Sep. 1, 1992.

BACKGROUND OF THE INVENTION

The present invention relates generally to methods and apparatus for therapeutic treatment and/or monitoring of functions of the human or animal body, in part by means of the efficient transmission or delivery of electrical signals between a therapeutic or monitoring system, such as an automatic implantable cardioverter/defibrillator, and the tissue or blood of the body, such as that of the heart, via one or more implanted electrodes. More particularly, the invention is directed to improvements in the configuration, energy transfer efficiency, therapeutic and sensing effectiveness, and implantation techniques of such implantable electrodes, especially for purposes of defibrillation, and which in the preferred applications are composed of carbon fibers or carbon-coated metallic fibers, for stimulating or sensing electrical reactions in body tissue and especially heart tissue.

Many parallels exist between the cardiac therapy provided with implantable defibrillators and the cardiac therapy provided with implantable pacemakers. At the outset of the use of each of these devices, problems were encountered in implantation of the device including therapy-delivery leads and even in application of the therapy for the benefit of the large numbers of patients who were identified as real candidates for such treatment.

In the case of cardiac pacing, the implant procedure itself was the major obstacle. Further, the technology was relatively primitive at its beginning, which precluded a more wide-spread use including prophylactic use for patients whose needs were not perceived as crucial but who, on the basis of prognosis, could derive benefit from the availability of demand-type pacing therapy.

The same situation exists for defibrillation therapy today. Difficult implant procedures such as open chest surgery necessitated for epicardial patch electrodes, coupled with the large size and relatively high cost of the devices, and the complex medical procedures associated with the implantation and difficulty of follow-up procedures for the patients, place serious limitations on the number of patients who can actually be addressed by the therapy in contrast to the significantly larger number of current patients who could benefit from implanted defibrillators for cardioversion and defibrillation of the heart.

While problems encountered with implantable defibrillators are somewhat ameliorated by the now growing clinical use of transvenous defibrillation leads, the current need for high energies to defibrillate the heart dictate capacitor and battery sizes that continue to mandate a rather uncomfortable device with a size and a weight unpleasant to patients. It follows that the major contribution to a more widespread use will be a substantial reduction in device size and weight and by facilitation of the implant procedure.

To reduce the size of the defibrillator, it is necessary to considerably reduce the energy required to defibrillate the heart (the so-called defibrillation threshold DFT). Current devices require more than 32 joules of energy, and even with further optimization that might be achieved with current lead and patch technology, in the majority of cases a DFT of 18 or more joules would still be needed. Defibrillation thresholds of that magnitude mean that despite improvements in implant technology, such as in capacitors and other larger-sized components and higher packing density in the devices, the device size and weight may only be reduced to a minor extent. The major breakthrough will only result from a considerable reduction in DFT.

Studies conducted by a research group with which the applicant herein is associated have revealed that the use of new low-polarization fiber materials for the defibrillation electrodes, such as are described in the '089 patent and the '173 application, considerably increase the effective electrical surface over the actual geometrical surface of the electrode. The result can be a significant reduction in DFT.

Of course, microminiaturization of electronic components has brought about considerable size reduction of implantable medical devices adapted to monitor and/or deliver electrical indicia and/or stimuli (broadly, electrical signals) within the body to detect or stimulate selected biological processes. Implantable defibrillators are broadly capable of monitoring and controlling cardiac activity as necessary to detect and alleviate arrhythmias or dysrhythmias such as fibrillation (both atrial defibrillation (AF) and ventricular fibrillation (VF)), pathologic tachycardia, and, in some instances, bradycardia. These devices respond automatically to sensing the dysrhythmia of interest to restore normal, regular cardiac rhythm by delivering electrical stimuli in the form of pulses, shocks or more complex waveforms to the atrial or ventricular cardiac tissue, as appropriate.

The invention described in the '089 patent is an improvement in defibrillating or cardioverting electrodes for automatic implantable defibrillators. The prior art had taught implanting patch electrodes to produce an electric field extending from one side of the heart to the other, e.g., through the ventricles, or a combination of an epicardial patch or patches and an endocardial counter-electrode implanted transvenously. Implantation of external patch electrodes had required a thoracotomy, which is highly invasive and requires a long recovery period.

An article titled "Clinical experience, complications and survival in 70 patients with the automatic implantable cardioverter/defibrillator", *Circulations*, vol. 71, no. 2, 1985, pp. 289-296 (D. Echt et al.) surveys complications associated with implantation of epicardial patch electrodes.

Another piece of prior art of interest is U.S. Pat. No. 4,774,952 which describes a multiple electrode structure that concentrates current in selected areas of the heart during defibrillation.

Problems persisted in attempts to interface electrodes with body tissue to attain a combination of low resistance conductivity, large surface area, low polarization and low intrinsic stiffness, while providing long-term communication of electrical signals and relatively high current levels. The implantation and manipulation of prior art electrodes remained complex procedures, particularly those employed for defibrillation, and were not very successful. A principal reason was the inefficient energy transfer between the electrode and excitable tissue (i.e., tissue having cell membrane field strength which can be stimulated electrically to produce cell depolarization).

Energy transmission and transfer between pacemaker electrodes and the heart has received considerable attention (see, e.g., survey article of Ripart and Muciga titled "Electrode heart interface: definition of the ideal electrode", in *PACE*, vol. 6, March 1983, pp. 410–421). Encouraging results may have been obtained using low polarization materials such as platinum, iridium and pyrolyzed carbon in the electrode tip having average surface area of 10 mm$^2$ (square millimeters), for stimulation with pacing pulses ranging from 2.5 to 5.0 volts, and for sensing cardiac activity. But cardiac pacing electrode requirements are manifestly different from defibrillation electrode requirements, which involve application of shocks with amplitudes of up to many hundreds of volts and over electrode surface areas of perhaps 10,000 mm$^2$.

German Democratic Republic patent 26 32 39 of Oct. 30, 1987 disclosed a pacing lead composed of a bundle of anisotropic carbon fibers. The electrode structure may be effective for pulse transmission along its longitudinal axis, but its relatively tiny point contact surface areas at the tissue interface and the tendency of the electrode interface to erode over time make it incapable of providing the large surface area required for defibrillation. Transfer of adequate energy from defibrillating pulses of from 500 to 2,000 volts typically required patch electrode surface area of from 50 to 100 cm$^2$ (square centimeters) to avoid possible local burning of the tissue, and transvenous electrode surface area of from 4 to 20 cm$^2$ for uniform energy flow through the heart.

The invention disclosed in the '089 patent provides a defibrillating electrode of low energy consumption, low polarization, flexibility to avoid mechanical restriction of the heart during beating, and ease of implantation. Implantation is performed without thoracotomy, long patient recovery time, pericardial hemorrhaging, potential infection, or complications attributable to adhesions from prior surgery where the patient is undergoing electrode replacement. Simplified implantation also reduces hospital costs by eliminating a need for specialized open heart surgical facilities and attending personnel.

According to the '089 patent, the electrode is composed of flexible, nonmetallic, electrically conductive, uninsulated fiber strands possessing isotropic conductance characteristics to form an improved electrical interface with body fluid (e.g., blood) and/or excitable tissue when the lead assembly is implanted into the body. Improved energy transfer and electrical communication across the electron-ion interface between the electrode and the blood/tissue, formed along the entire length of exposed surface of each fiber rather than at restricted point contact areas, are attained. The isotropic property assures electron conduction substantially equally in all directions, thereby expanding the electron-ion boundary.

By utilizing a multiplicity of such fibers in the electrode, its effective electrical surface area is many times larger than its actual geometrical surface area. The fibers allow the electrode to be configured in a size and shape suitable for the interface at the selected implant location.

Other prior art relevant to the '089 patent invention includes the following. U.S. Pat. No. 4,574,814 (Buffet) describes synchronous pacing in chambers of different size, using resiliently deformable carbon fibers which assume a "feather duster" shape with fiber ends providing an envelope of contact of myocardial tissue to increase the area of anchoring, and point contact of non-isotropic fibers with the tissue for excitation and anchoring. An article titled "Carbon Fibers as an Electrode Material" (Starrenburg et al.) in *IEEE Transactions on Biomedical Engineering*, vol. BME-29, no. 5 (May 1982), at pp. 352 et seq., describes a flexible carbon fiber bundle electrode having a short segment of straight bare fibers between two insulated regions for muscle stimulation, but notes that the electrode suffered breakdown during electrical pulse testing and as a result of mechanical stresses when implanted. An article titled "New Plastics That Carry Electricity" in the Jun. 18, 1979 issue of *Newsweek* magazine describes the possible use of polyacetylene plastic doped with chemicals to enable it to carry electric current, as a pacemaker lead wire.

Great Britain patent No. 1,219,017 (Thomson Medical-Telco) describes an electrical conductor of braided ,non-isotropic, carbonized fibers as a lead for cardiac pacing, which is insulated along its entire length except at an end for point contact excitation of tissue. U.S. Pat. No. 4,506.673 (Bonnell) describes electrical tissue growth stimulators in which a non-isotropic mesh of biodegradable, electrically conductive, carbon particle-impregnated cotton fibers provides cathodic and anodic stimulation. U.S. Pat. No. 4,198,991 (Harris) describes a cardiac pacing lead with carbon filaments covered by an insulating sheath except at the lead tip the form a brush-like electrode structure for point contact of tissue.

The '173 application discloses a patch, tube or other mesh of individually woven isotropic carbon fibers or metallic fibers coated with isotropic carbon employed as an electrode for cardioversion or defibrillation. Such electrodes impregnated with anticoagulant substance or pharmacologic agent, such as heparin or hirudin, prevent blood clotting or platelet formation along the fibers which would decrease the efficiency of the electrode in energy transfer vis-a-vis the cardiac tissue to be stimulated.

Such isotropic carbon or carbon-coated metal fiber defibrillation electrodes may be implanted with minimal invasive surgery, as by a puncture opening in the abdomen or chest wall. Electrode insertion is made with a puncture needle and associated introducing catheter, into the pericardial sac for positioning adjacent the epicardium. A braided conductive fiber (carbon or carbon-coated) tube, preformed into a flat coil configuration, is readily inserted through the puncture using a stiffening wire.

To further improve the implantation and operation of these defibrillator devices, it is desirable to make use of the defibrillator can (i.e., the metal housing of the implantable waveform generator) as one of the electrical poles of the overall therapy delivery system, and predominantly as the anodal pole. In this way, a right ventricular defibrillation lead which is implanted completely transvenously and without major surgery, similar to a implanting a pacing lead, acts as one of the electrodes, and the defibrillator can acts as the second electrode. Although this will facilitate implant technology and surgical requirements considerably, it will not measurably reduce the size and cost of the devices.

It is a principal object of the present invention to provide means for adequately reducing the defibrillation threshold without the need for major surgery, and in that respect, to provide an implantable defibrillator having a weight of approximately 50 grams which would therefore be much better matched to patient need and comfort.

It is a further object to reduce the cost of the device and its implantation. This is an important consideration in view of the increasing concern over health care cost.

SUMMARY OF THE INVENTION

According to the invention, the right ventricular electrode is transvenously implanted in the manner of the current state of the art, and the defibrillator can is used as the second pole for defibrillation. To achieve an acceptable vector throughout the heart with application of the defibrillation shock waveform, the defibrillator can (waveform generator) is implanted in the left pectoral region by means of an incision in the skin and preparation of the pectoralis muscle's fascia. The lead is implanted via the same incision through the subclavian or cephalic or external jugular vein.

According to a principal aspect of the invention, the effectiveness of the metallic can of the defibrillator is considerably increased by surrounding the defibrillator can with a conductive pouch comprising a net of electrically conductive fibers, preferably of very fine electrically conductive carbon fibers. This increases the effective size of the electrical surface of the defibrillator can, and the greater the conductive surface, the greater is the effectiveness of a defibrillating shock.

The electrically conductive pouch is placed about the defibrillator can before the defibrillator waveform generator is implanted into the body, in a manner to establish good electrical contact between the metallic can and the conductive pouch. One or more fixation mechanisms are utilized to secure the pouch to the can, and the assembly is then inserted into the preformed pocket in the patient's body and affixed to the patient's body by suitable fixation means to prevent migration of the device.

The field strength of the shock waveform, which is critical for defibrillation, is a function of the electrically conductive surface of the pouch and of the distance of the combined pouch/can electrode to the heart. Therefore, another aspect of the current invention is to use the electrically conductive pouch as a connector, and to connect the pouch to an electrically conductive carbon braid as a lead or electrode extension for transporting the defibrillation energy to a desired region. The carbon braid is formed as a tubular lead starting at the very bottom of the pouch.

In the preferred embodiment, this fine, tubular electrode extension has a diameter of 7 french, equaling about 2 millimeters, and is subcutaneously tunnelled to the area of the apex of the left ventricle. This means that in a subcutaneous position, the fine lead extension runs downwardly parallel to the sternum, but outside of the thoracic cage. The procedure is easily performed by applying a second cut at a location where the lead extension must end, close to the apex of the left ventricle but outside the thoracic cage. With this small incision, from about 0.5 centimeter to 1 cm long, a forceps or an introducer sheath may be pushed subcutaneously in the direction of the pocket in which the defibrillator waveform generator is to be embedded.

The electrically conductive braided electrode, after being connected to the pouch, is pulled down in the subcutaneous location and fixed to the connective tissue, fat and muscles. Because of this location of the braided electrode extension, the shock waveform energy from the defibrillator is applied closer to the heart, and the electrical field strength is increased considerably over that which would be present using the can alone as an electrode. Additionally, this subcutaneous carbon lead extension may be used as a sensing electrode. Electrocardiographic (ECG) morphologies indicating different heart conditions such as ventricular tachycardia or ischemic conditions, as well as heart rate, are detected more easily from this lead.

According to a further aspect of the invention, the portion of the lead extension down to the heart is electrically insulated, especially in close proximity to the conductive pouch. As a result, the electrical concentration of current and of the electrical field is enhanced in the immediate vicinity of the heart.

Depending on the size and functioning of the heart, especially the ejection fraction and volumes of right and left ventricle, there are some patients that exhibit too great a DFT to be treated with a defibrillator of small size and low energy. If it is assumed that the highest acceptable threshold for a patient supplied with such a device is 8 joules or less, a maximum shock energy of 16 joules will be sufficient to guarantee a 100% safety margin.

In cases where a DFT as low as 5 to 8 joules cannot be achieved, a solution according to the invention is to use the same arrangement of an electrically conductive pouch with the connected tubular electrode (lead) extension implanted subcutaneously and by puncture surgery between the ribs into the pericardial space. In this case, the primary carbon electrode extension is made much longer than is needed for subcutaneous application only. The penetration of the pericardial space further reduces the DFT, beyond what can be achieved by the subcutaneous extension alone. Puncturing or other minimally invasive surgery such as by a small surgical incision in the area of the xiphoid of the sternum is used to place the electrode extension in closer proximity to the heart. If a longer electrode extension is provided than is necessary according to a DFT determination for a particular patient, so that the pouch and subcutaneous lead alone will yield acceptable thresholds to achieve defibrillation, the unneeded part of the distal end of the electrode extension may be severed by the surgeon just prior to the actual subcutaneous implantation.

Experiments conducted by a research group with which the applicant is associated have shown that by means of the small braid of fine electrically conductive fibers connected to the pouch, a very low DFT can be achieved. Indeed, the observed DFT is more than 50% lower than DFTs observed using conventional epicardial patch electrode technology, which has heretofore been deemed to be the standard. Therefore, the use of an electrically conductive pouch and lead extension connected to it, both consisting of the same type of electrically conductive material, may be used in a staged therapy depending on the outcome of DFT testing with the initial procedures.

BRIEF DESCRIPTION OF THE DRAWINGS

The above and still further objects, aspects, features and attendant advantages of the present invention will be better understood from a consideration of the following detailed description of the best mode presently contemplated for carrying out the invention, by reference to certain presently preferred embodiments and methods thereof, taken in conjunction with the accompanying drawings, in which.

DESCRIPTION OF THE PRESENTLY PREFERRED EMBODIMENTS AND METHODS

The conductive pouch of the invention utilizes a fiber electrode structure of the types disclosed in the '089 patent and the '173 application. Such structures provide a low polarization, low capacitance, low resistance and low impedance electrical interface with contacting body fluid and/or adjacent excitable tissue. These structures are preferably fabricated from a multiplicity of uninsulated, individual, substantially isotropic electrical current conducting fibers, which are maintained in a flexible configuration adapted to form the electrical interface along an entire substantial length of electrically uninsulated surface of the configuration. The configurations are shaped and sized to be easily positioned at the selected site of the electrode in the patient's body. A multiplicity of the interwoven fibers provide an effective surface area for the electrical interface which is considerably greater than the actual geometrical surface area of the electrode.

Flexibility of the configuration may be maintained by the interweaving of the fibers, to produce substantially two-dimensional or three-dimensional shapes. Substantially isotropic, electrically conductive carbon, carbon derivative or carbon-coated metallic fibers used for the conductive pouch configuration preferably have thicknesses less than about 40 microns (i.e., micrometers, or $10^{-6}$ meter).

Electrically conductive polymers are described, for example, by Dr. Herbert Naarmann of BASF in "Elektrisch leitfähige Polymere: Anwendungsspektrum noch nicht ausgereizt", *Chemische Industrie*, no. 6/87, and in "Die elektrochemische Polymerisation", *Angewandte Makromolekulare Chemie* 162, 1988, pp. 1-17. U.S. Pat. No. 4,468,291 describes a method for producing electrically conductive polypyrrole films.

Among the materials useful for fabricating the fiber electrodes are iodine-doped polyacythylene fibers, which have a conductivity of more than 100,000 siemens per centimeter, sometimes with a high degree of crystallinity; polypyrrole polymer; and carbon or C fibers obtainable from the Celion Company with diameters of 20 microns as thin fiber strands which may be woven together.

In these electrically conductive carbon derivatives, the addition of electron donors or acceptors and the reduction of oxidation of the matrix produce a transition from electrically insulative to electrically conductive properties, with a perceptible increase in electron mobility and conductivity. These polymers have conductivities of up to 100,000 siemens per cm and possess the property of producibility in very fine fibers, with thinness in the range from 8 to 20 microns. A bundle of these small diameter fibers presents a very large effective surface area - - - for example, 10 $cm^2$ per cm of bundle length for a fiber bundle 2 millimeters in diameter with individual fibers of 12 microns thickness.

Additionally, these polymers are flexible, and are biologically inert because of their carbon composition. They exhibit a smooth exterior surface and possess reasonable non-thrombogenic characteristics which tend to reduce foreign body reaction, as has been confirmed in use of other types of carbon implants, as in bone surgery. The fibers are readily formed into various configurations, such as woven together, woven into small chains, bundles or tubes, or formed into a netting, which is appropriate for a conductive pouch.

Rather than using carbon or electrically conductive polymers of this type, metallic fibers may be employed, of diameters in the range of, say, 10 to 30 microns, to create the desired large effective surface area electrodes. A suitable metallic electrode fiber, for example, is iridium platinum multistrand wire composed of nine strands of 0.0011" (about 27 microns) 10% iridium-90% platinum bare wire available from Sigmund Cohn Corp. of Mount Vernon, N.Y. as part number 10Ir9/49B. The multistrand wire may be braided to form larger bundles, meshes or nets.

Preferably, the metallic fibers or strands are coated with carbon to coating thicknesses starting as low as molecular layers in the nanometer range and up to about 10 microns. This provides the fibers with features and characteristics similar to those of pure carbon polymer fibers, but with the advantage that solid electrical connection is readily made between these coated metallic fine fibers and a low resistance, conductive lead wire (DBS wire, for example) by electro-welding, with only about 0.3 ohms per contact, to carry the defibrillation energy to the braid. A carbon material suitable for use in such coating is polyvinyl pyrrolidone, which can be applied to the metal strands or fibers by electro-galvanization, or other suitable process such as that disclosed in German patent application P 36 07 302.4. Applying a carbon coating using an electrolytic process allows the thickness to be carefully controlled, according to such factors as length of time in the bath, magnitude of current, and so forth.

The DBS conductive wire lead may be formed into a helical coil which provides a central opening for a stylus. An uninsulated portion of the wire is brought into electrical contact with a portion of the braid from which the carbon is removed, thereby exposing the metal fibers, which may then be electrically welded to the lead. Molded silicone insulation is then applied over the junction to prevent moisture from penetrating. The benefits of good electrical connection by virtue of the metal to metal contact and electro-welding, together with the large effective surface area of the electrode and consequently permissible small actual size of the lead (4 or 5 french), exceed those of the fibers composed purely of the carbon derivatives. This is primarily because the polymer fibers must be crimped, the contact pressure is critical, and they cannot be welded. The electrical connection to the latter type of fibers can be made by application of a conductive epoxy which makes contact with the carbon.

A conductive pouch for receiving the metallic can in which the waveform generator or stimulus generator of the implantable defibrillator is housed is readily formed by interweaving the fibers into a netting having a suitably sized opening for the can. Preferably, the interwoven fibers of the tubular transvenous electrode cross over and under each other to permit expansion and contraction of the configuration with movements of the patient.

Figure 1:
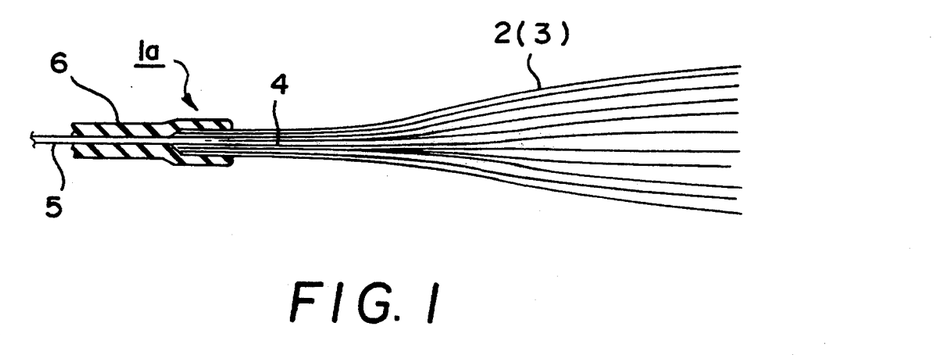
FIG. 1 is a side view, partly in section, of a fiber electrode including conductive fibers preferably used in an embodiment of the invention.

Various fibers and fiber structures for use in conductive pouch structures in conjunction with implantable therapeutic medical devices such as an automatic cardioverter/defibrillator are illustrated in the Figures, and are not intended to be shown to scale. In FIG. 1, a fiber electrode 1a includes a plurality of electrically conductive fibers 2 or fiber strands 3 (shown in cross-section in FIG. 4) which are compacted together at one end to form a short rod-like configuration 4 for electrical connection to an electrical lead 5. Electrical insulation 6 surrounds the point of connection and may extend for a portion or the entire length of the lead. Along the uninsulated length, the fiber structure provides a large effective area of electrical interaction with blood and tissue, owing in part to the multiplicity of fibers each having its own surface area and to the isotropic property of the fibers.

Figure 2:
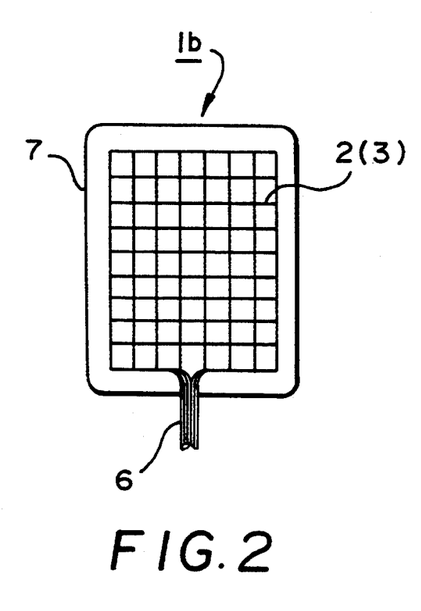
FIG. 2 is a plan view of a two-dimensional patch or pad electrode woven from fibers of the type shown in FIG. 1.
Figure 4:
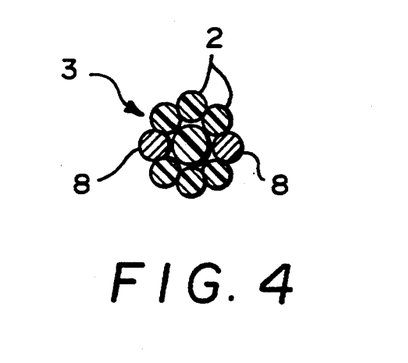
FIG. 4 is a cross-sectional view of an electrically conductive fiber bundle or filament in which some of the fibers are markers opaque to X-ray or fluoroscopic radiant energy, for viewing during certain implantation procedures.

FIG. 2 illustrates a flat two-dimensional electrode structure 1b which is woven with bundles of fibers having a plurality of individual fibers 2 or strands 3, as in FIG. 4. The fibers may be electrically connected to an electrically conductive lead 6. Insulation may be provided over any desired portion of the length of the lead by applying a flexible electrically insulating carrier 7.

Figure 3:
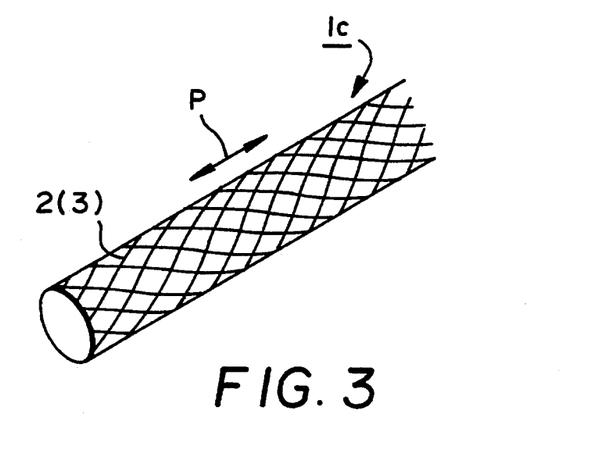
FIG. 3 is a perspective view of a portion of a three-dimensional tubular electrode woven and braided from conductive fibers, which may be used as an extension lead according to the present invention.

In FIG. 3, a three-dimensional configuration suitable for an extension lead 1c as utilized in the invention (as will be described below) is woven from individual fibers 2 or strands 3. By virtue of its flexible fiber construction, the configuration may be made to conform to a tortuous path for purposes of implantation. The non-thrombogenic and anti-inflammatory property of carbon fiber material helps to avoid an early buildup of tissue on the electrode surface which would otherwise tend to reduce its efficiency as an electrode material for establishing an electric field during defibrillation.

An implanted electrode may exhibit an acceptably small acute threshold, but an overly great chronic threshold, the increase occurring only gradually over several weeks as a result of fibrous tissue growth from thrombosis and foreign body reaction. This reduces the electric field and energy transfer efficiency across the heart tissue during delivery of the desired shock waveform for defibrillation or cardioversion. To prevent this, heparin, hirudin, steroids or other antithrombotic, anti-inflammatory or anticoagulant substances may be impregnated into the surface of the fibers to molecularly bond therewith. Carbon will remain impregnated indefinitely with such substances, with only minor solving into the blood over time.

Such impregnation of the anticoagulant substances may be performed by known procedures to achieve bonding of the molecules to the fiber structure, such as the electrochemical process described by Dr. H. Naarman of BASF in the article referenced above.

An important consideration in defibrillation therapy is relatively uniform distribution of the electric field through the mass of cardiac tissue between the electrodes. Theoretically, the distribution would be optimum if the implant site of the electrode were sufficiently remote from the heart, such as a site in the patient's leg - - - but such positioning would produce much too weak a field because of the great distance from the heart. The most realistic theoretical approach would be to cover the entire outside of the heart, and then defibrillate against an electrode inside the heart. This would also produce a nearly uniform field distribution, with the added advantage of high field strength. Defibrillating from outside to inside the heart is energy efficient not only because it produces the desired virtually equal distribution of the field, but also because the blood in the heart is an excellent conductor.

Nevertheless, it is desirable in view of both surgical and patient considerations to seek to strike a compromise between the theoretical and the practical aspects. In practice, the application of large area electrodes around the heart is a difficult procedure for even the most skilled surgeon, and using conventional techniques, is highly invasive and traumatic to the patient. On the other hand, if the defibrillation threshold can be held as low as approximately five joules, and maintained so that it does not increase significantly over time, a much easier and effective approach is to use a single transvenous lead carrying at least one electrode, together with the metallic can of the waveform generator as another electrode. The can electrode is considerably enhanced by means of a surrounding conductive pouch according to the invention. Both the acute and chronic thresholds should be maintained at extremely low levels.

Figure 5:
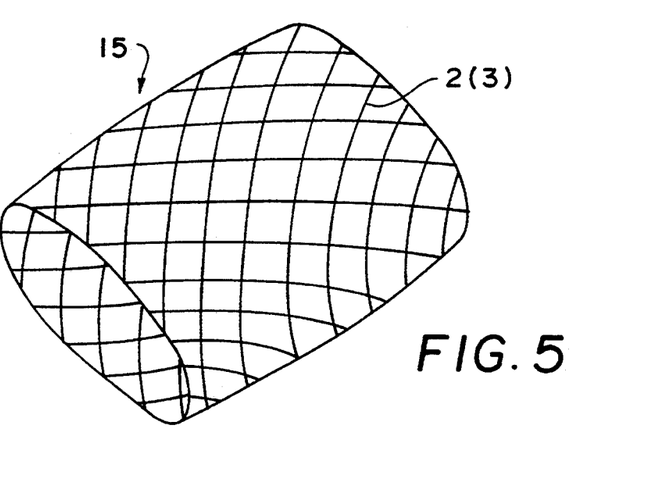
FIG. 5 is a perspective view of a three-dimensional pouch electrode woven from conductive fibers, according to the present invention.

In FIG. 5, a three-dimensional configuration suitable for a conductive pouch 15 as utilized in the invention is woven from individual fibers 2 or strands 3. By virtue of its flexible fiber construction, the configuration is readily adapted to conform closely to the size and shape of a range of waveform generator cans, and to encompass and make good electrical contact with the metal structure of the can. Here also, the carbon fiber material has non-thrombogenic and anti-inflammatory properties, and an anti-coagulant agent may be applied to the fiber surface to improve its resistance to formation of connective tissue on the surface.

In essence, the conductive pouch 15, when in use on the metallic can of the waveform generator of an implanted defibrillator, serves as an electrical connector for the extension lead in a manner to be described presently, which is quite independent of any plug or connector size or shape that typically present restrictive limits in other connector structures.

Figure 6:
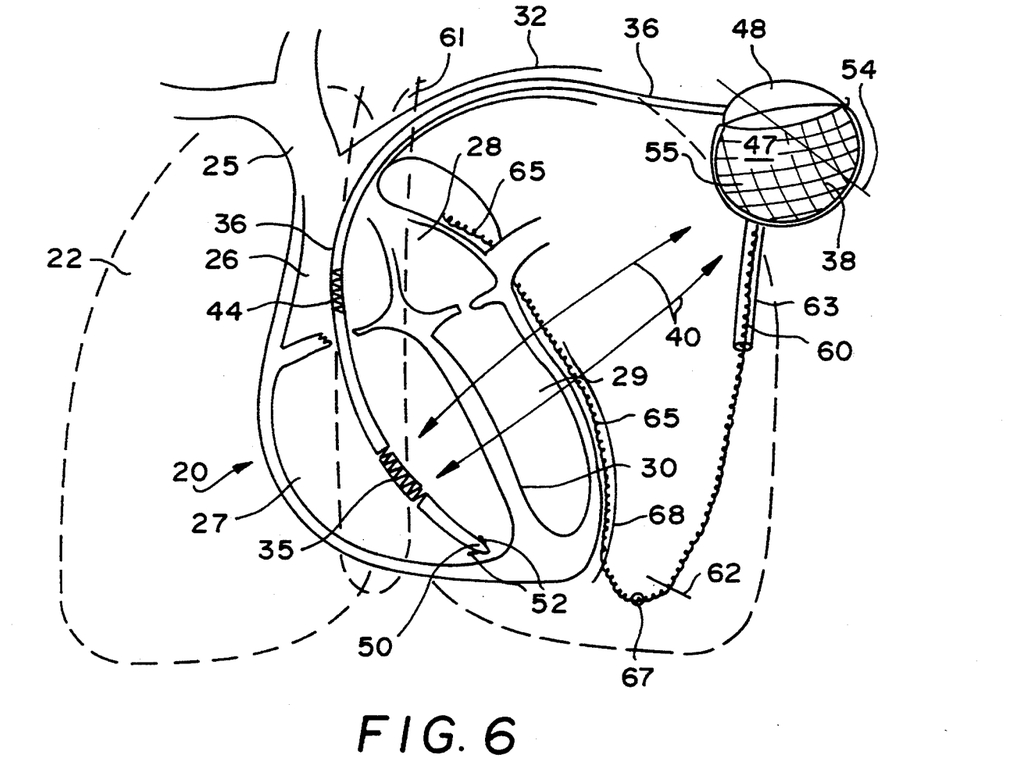
FIG. 6 is a simplified, partial perspective view of the patient's chest, sternum, heart and lungs illustrating the placement of various components of an implanted defibrillator using conductive fiber pouch and extension lead electrodes of the invention.

Referring to FIG. 6, the patient's heart 20, lungs 22 (in simplified outline) and overlying chest area, superior vena cava 25, right atrium 26, right ventricle 27, left atrium 28, left ventricle 29, septum 30, and left subclavian vein 32, are generally disposed as indicated. The desire is to create a considerably higher energy density to the septum and left heart structures than can be achieved with a conventional electrode placement. Assume that a defibrillating shock or lower level cardioverting impulse is delivered between an electrode 35 positioned in a right chamber (ventricle 27) of the heart on a transvenous lead 36, and the electrode provided by the metal can 38 that houses the electronics of the waveform generator of the implanted defibrillator. The resulting electric field vectors (path of the current) are illustrated for the sake of simplicity and clarity by double-headed arrows 40. The field encompasses a greater portion of the heart structure, particularly the septum and left and right ventricular mass. A significant problem is that the lung has a high specific resistivity, on the order of 1000 ohms per centimeter, which results in a dramatic drop in field strength across that region. Additionally, the heart is anisotropic, i.e., its conductivity and conduction velocity for current flow is considerably greater (about 3.5 times) along its vertical axis, approximately along the septum, than it is along the horizontal axis.

With reference again to FIG. 6, defibrillator waveform generator 47 is housed in metallic can 38 implanted in the left pectoral region of the patient. The metallic can has a single connector 48 mounted on it. A plug at the proximal end of transvenous lead 36 is inserted into the single receptacle of connector 48 for electrical connection of the lead conductors to a predetermined point in the internal circuitry of the generator. It will be understood that reference to "waveform generator" or "stimulus generator" in the specification or claims is used in the broad sense of a programmable device including means for sensing cardiac electrical activity (and/or other physiologic parameter), or for processing an electrical signal indicative of such sensed cardiac activity (or other physiologic parameter), and for generating a waveform or waveforms according to the selected therapy regimen to be delivered to the patient's heart.

Transvenous lead 36 is a bipolar lead having a pacing and sensing tip 50 at its distal end for placement inside the apex of the right ventricle 27, with passive or active retention means such as tines 52 at or adjacent the tip to engage trabeculae in the ventricle. The transvenous lead is shown here as being implanted through the patient's left subclavian vein 32. A braided tubular portion of a conductor in lead 36 is composed of a multiplicity of tiny conductive carbon fibers or metallic wires (coated or uncoated with a surface layer of carbon), as previously described, and is arranged and adapted to be located in the right ventricle when the tip is seated for capture, to act as a transvenous atrial defibrillation electrode 44.

After connection of the plug of lead 36 into the receptacle in connector block 48, defibrillator waveform generator 47 is implanted in the patient's body, preferably by insertion into a pocket formed in the left pectoral region of the patient's chest via an incision 54.

According to the invention, electrically conductive pouch 55 is disposed about and electrically connected to the waveform generator 47. This electrical connection is provided by the electrical contact between the pouch and the metal can of the generator, and hence, is independent of any nature or type of connector receptacle or plug. Therefore, only one receptacle is required for the connector block 48, and that is solely to accommodate transvenous lead 36. Additionally, the pouch 55 makes electrical connection with the generator can 38 irrespective of generator manufacturer or the size and dimensions of the can, within an appropriate range suitable for the dimensions of the pouch.

In the preferred embodiment, the pouch 55 comprises a woven net or mesh of multiple filaments of fine, electrically conductive, uninsulated fibers of a type described above, the net being arranged and adapted to receive and envelop the metallic can 38 of the defibrillator waveform generator, or at least the majority of the can. The electrically conductive fibers are preferably composed of isotropic carbon, a low polarization material which enables the pouch to significantly enhance the electrical properties of metallic can 38. Alternatively, the fibers may be composed of tiny wires of platinum-iridium alloy, and in that case, are preferably coated with a surface layer of isotropic carbon to reduce polarization. All of these fiber types have been described in greater detail above. Such a conductive pouch electrode itself serves to enhance the electric field during defibrillation of the patient's heart.

The net 55 may also be electrically connected, by means described earlier herein, to the proximal end 58 of a fine tubular braided extension lead 60 (such as is shown in FIG. 3) which is implanted subcutaneously to run downwardly from the pouch, parallel to the patient's sternum and heart. The extension lead 60 is composed of the same type of tiny, individual, uninsulated, predominantly isotropic, conductive carbon or metallic fibers as the conductive pouch 55. If platinum-iridium alloy wires are used, each individual fiber is preferably a bundle of nine wires each of approximately 27 microns in diameter to form a primary filament of about 80 microns, which is braided together with other such filaments to form a tubular configuration. Here again, such metallic fibers are preferably coated with carbon to reduce polarization.

Subcutaneous implantation of the fiber extension lead 60 is accomplished by inserting it into the subcutaneous position via a pair of incisions 54, 62. Incision 54 was made to form the pocket for the waveform generator. After incision 62 is made, an introducer sheath (not shown) of appropriate diameter and length is introduced through that incision and pushed through the subcutaneous tissue over the ribs and muscles towards incision 54. There, the distal end of the extension lead 60 is affixed to the tip of the introducer, and the introducer sheath is then withdrawn from incision 54 towards incision 62, to bring the extension lead 60 into the subcutaneous position. The proximal end portion of extension lead 60 may be insulated by a small segment of silicone (or other biocompatible material) tubing 63 applied to the outer surface of the lead. The silicone tubing serves to intensify the electric field and the vector for defibrillation between right ventricular electrode 44 and the uninsulated (electrode) portion of extension lead 60. This assures desired concentration of electrical energy to defibrillate the heart during application of the shock waveform from the waveform generator in response to detection of fibrillation.

As noted above, it is desirable to provide a field which avoids the drop across the lungs and takes advantage of the anisotropy of the heart. This is precisely the effect achieved with an electrode pole in the right ventricle (as at 35) or the right atrium (as at 44) and the can/conductive pouch electrode 38/55, particularly with the presence of subcutaneous extension lead 60.

Here, a strong, substantially uniform field is achieved, with the field direction again denoted by double-headed arrows 40 in the case of the right ventricular electrode 35 and the pouch with its extension lead, encompassing the left as well as the right side of the heart, and with a strong vertical component.

In certain cases, such an arrangement utilizing the conductive pouch 55 and the electrically connected, wholly subcutaneously implanted extension lead 60 may not yield an acceptable defibrillation threshold. In such cases, an elongated extension lead 60 may be utilized so that its distal end 65 is sufficiently long for introduction into the pericardial sac. This introduction may be accomplished by means of minimal invasive surgery such as a puncture through the patient's thoracic cage at a point 67, followed by endoscopic insertion into the pericardial sac 68, preferably closely adjacent to the left ventricle 29 to optimize the electric field strength through the ventricular mass and the septum during defibrillation. The distal end 65 of extension lead 60 is used as the electrode for defibrillation in considerably closer proximity to the heart than was the case with the wholly subcutaneous implantation of the extension lead. Placement of distal end 65 inside the sac 68 improves the effectiveness of the defibrillating shock when delivered in response to detection of fibrillation.

In those cases, extension lead 60 is preferably insulated by tubing 63 throughout its subcutaneous length up to incision 62 (as shown by the phantom lines, so that the insulated portion of extension lead 60 serves only as an electrical conductor for the distal end 65 of the lead, which becomes the defibrillation electrode from the generator can.

When the fiber extension lead is implanted by puncture surgery or the like, the chest/abdominal wall is punctured, and then the pericardial sac is punctured, using a needle. Then a fine guide wire is introduced into the pericardial space adjacent to the beating heart. The needle is removed and an introducing catheter and dilator are inserted via the guide wire. The fiber bundle is then introduced through the lumen of the catheter, and the catheter is withdrawn to leave the electrode in position between the pericardium and the myocardium for connection via an electrically connected lead to an implanted defibrillator. The patient's ECG may be monitored when the pericardium is punctured, to observe whether and when the puncture needle (which, in that instance, is connected to an ECG amplifier) contacts the heart. Such contact is clearly visible from the reaction of the ECG, and when it occurs the needle is withdrawn slightly to allow introduction of the catheter and the electrode.

While the puncture needle is inserted into the patient's body at puncture site 65 and the needle is guided into the space between the pericardium 68 and the heart 22, the procedure is monitored by X-ray, fluoroscopy or, preferably, endoscopy. A guide catheter is inserted into the body over a guide wire, and an interior dilator is used to expand the passageway through the puncture site and the pericardial sac. The catheter may be bent slightly in its anterior region to permit easier positioning of the extension lead when implanted. After removal of the dilator, the fiber extension lead is inserted through the guide catheter and properly positioned within the pericardial sac. The introducer sheaths for the guide catheter may be of known peel-away type for rapid removal.

For precise placement of a polymer fiber electrode by X-ray, fluoroscopy or endoscopy, the fibers may be interspersed with fibers composed of material opaque to radiation of the type employed for viewing the progress of the implantation procedure from a point external to the body. The opaque fibers or strands 8 are interposed among the polymer fibers 2 as shown in the cross-sectional view of FIG. 4. Alternatively, the polymer fibers themselves may be doped or coated with materials impenetrable to such radiant energy. If the fibers are metallic, whether bare or carbon-coated, they are opaque and readily visualized during the implant procedure.

Atrial defibrillation may be provided by implanting electrode 44 in the right atrium using the same transvenous lead 36 but a different conductor from that used for the ventricular electrode 35. For purposes of atrial fibrillation, the distal end 65 of the extension lead may be inserted further into the pericardial sac in proximity to the left atrium 28 to intensify the electric field through the atrial mass and the septum during defibrillation.

The procedure can be performed under local anesthesia, to avoid the need for general anesthesia. Defibrillation testing may be conducted with the patient subjected to very short acting neuroleptic agents, or tranquilizers, just as currently used for the testing of implantable defibrillators after implantation. This is done typically during the first so-called pre-hospital discharge tests. Medications used for this purpose include Valium (diazepam) and Dormicum, which are derivatives of the diazepam family. In future, then, implantation of defibrillators might be performed entirely without need for general anesthesia, which would make the goal of performing the implantation on an outpatient basis more likely.

Although certain preferred embodiments of the invention and methods of fabrication and implantation thereof have been described herein, it will be apparent to those skilled in the art from the foregoing description, that variations and modifications of the disclosed embodiments and methods may be made without departing from the true spirit and scope of the invention. Accordingly, it is intended that the invention shall be limited only to the extent required by the appended claims and the rules and principles of applicable law.

What is claimed is:

1. A defibrillator adapted for implantation in a patient's body, comprising:
   a waveform generator including a metal housing for electronic components of the generator, and
   an electrically conductive pouch having an effective electrical surface area considerably larger than its geometric surface area, said pouch receiving the generator and making electrical connection with said metal housing to enhance the conductivity of the housing as an electrode of the defibrillator when implanted in the patient's body.

2. The defibrillator of claim 1, wherein:
   said pouch is fabricated from a flexible array of generally interwoven electrically conductive fibers, said array constituting an electrical connector which is independent of plug and connector size and type of said waveform generator.

3. The defibrillator of claim 2, wherein:
   each of the fibers of said array has a carbon surface.

4. The defibrillator of claim 3, wherein:
   the carbon surface of each of the fibers of said array is impregnated with an antithrombin or anti-inflammatory substance to inhibit fibrotic growth at exposed surfaces of the pouch when implanted in the patient's body.

5. The defibrillator of claim 4, wherein:
the fibers of said array are composed of isotropic carbon.

6. The defibrillator of claim 4, wherein:
the fibers of said array are tiny individual elongate uninsulated metal wires having a surface layer of isotropic carbon.

7. The defibrillator of claim 6, wherein:
the metal wires are composed of a platinum-iridium alloy.

8. The defibrillator of claim 2, including:
an extension lead composed of a second flexible array of generally interwoven electrically conductive fibers electrically connected to the conductive fibers of the pouch.

9. A method for enhancing the effectiveness of an automatic implantable defibrillator having a metallic can which houses electronic components of a waveform generator of the defibrillator, and which is to be used as one of electrodes for defibrillation, the method comprising the steps of:
at least partially enclosing the metallic can within and in contact with an electrically conductive pouch having a substantially larger electrical surface area than its geometric surface area, to provide electrical connection between the pouch and the can, and
implanting the waveform generator with its metallic can at least partially enclosed by the pouch into a patient's body, to improve field strength and vector of an electric field through the patient's heart during defibrillation.

10. The method of claim 9, including:
selecting the pouch to be composed of a flexible array of generally interwoven electrically conductive fibers so that the array acts as an electrical connector which is independent of plug and connector size and type of said waveform generator.

11. The method of claim 10, including:
selecting the pouch in which the conductive fibers of the array have a carbon surface.

12. The method of claim 11, including:
selecting the pouch in which the carbon surface of the fibers is impregnated with an antithrombin or anti-inflammatory substance to inhibit fibrotic growth at exposed surfaces of the pouch when implanted in the patient's body.

13. The method of claim 11, including:
selecting the pouch in which the fibers of said array are composed of isotropic carbon.

14. The method of claim 11, including:
selecting the pouch in which the fibers of said array are tiny individual elongate uninsulated metal wires having a surface layer of isotropic carbon.

15. The method of claim 10, including:
implanting with the pouch an extension conductive lead running subcutaneously parallel to the patient's sternum and heart up to a distal end of the lead, and with the lead electrically connected at a proximal end to the pouch so that energy is transmitted from the generator can to the lead during defibrillation, to provide a source of energy in close proximity to the heart.

16. The method of claim 15, including:
selecting the extension lead to be composed of a second flexible array of generally interwoven electrically conductive fibers electrically connected to the conductive fibers of the pouch.

17. The method of claim 16, including:
selecting an extension lead in which the conductive fibers have a carbon surface.

18. The method of claim 17, including:
selecting the extension lead in which the carbon surface of the fibers is impregnated with an antithrombin or anti-inflammatory substance to inhibit fibrotic growth at uninsulated surfaces of the lead when implanted in the patient's body.

19. The method of claim 17, including:
selecting the extension lead in which the fibers thereof are composed of isotropic carbon.

20. The method of claim 17, including:
selecting the extension lead in which the fibers thereof are tiny individual elongate uninsulated metal wires having a surface layer of isotropic carbon to reduce polarization.

21. The method of claim 20, including:
selecting the extension lead in which the metal wires thereof are composed of platinum-iridium alloy.

22. The method of claim 21, including:
selecting the extension lead in which the metal wires thereof each have a diameter of approximately 27 microns and are twisted together to form a filament of 80 microns diameter with a plurality of such filaments braided together to form a tubular mesh.

23. The method of claim 16, including:
at least partly electrically insulating the extension lead to concentrate the electrical energy to the heart during defibrillation.

24. The method of claim 16, including:
implanting the distal end of the extension lead into the patient's pericardial sac endoscopically to lower the defibrillation threshold of the patient's heart by placing the distal end of the lead in closer proximity to the heart.

25. The method of claim 24, including:
insulating the extension lead over a substantial portion of the subcutaneous run of its length from the pouch to a point at which it is endoscopically implanted, to concentrate the energy more closely to the heart during defibrillation.

26. The method of claim 9, including:
providing said waveform generator with an electrical connector coupled to preselected electronic components of the waveform generator in said metallic can,
implanting a single transvenous lead with plural conductors and electrodes thereon positioned respectively in the atrium and ventricle on the right side of the patient's heart, and
connecting said single transvenous lead to said electrical connector to cooperate with said one electrode formed by said metallic can and the electrically conductive pouch connected thereto to enable selective defibrillation and cardioversion of the atrium and ventricle and to sense intrinsic electrical activity of the heart with said single transvenous lead.

* * * * *